US006645472B1

United States Patent
Anderson

(10) Patent No.: US 6,645,472 B1
(45) Date of Patent: Nov. 11, 2003

(54) ORAL HYGIENE POWDER COMPOSITION AND METHOD

(76) Inventor: Michael R. Anderson, 1355 W. Palmetto Park Rd. #129, Boca Raton, FL (US) 33486

(*) Notice: Subject to any disclaimer, the term of this patent is extended or adjusted under 35 U.S.C. 154(b) by 0 days.

(21) Appl. No.: 10/243,063

(22) Filed: Sep. 13, 2002

(51) Int. Cl.$^7$ .............................. A61K 7/16; A61K 7/26; A61K 35/20; A61K 7/20
(52) U.S. Cl. ................... 424/53; 424/49; 424/58
(58) Field of Search ...................... 424/49–58

(56) References Cited

U.S. PATENT DOCUMENTS

| | | | | |
|---|---|---|---|---|
| 2,470,906 A | * | 5/1949 | Taylor | 167/93 |
| 2,778,045 A | * | 1/1957 | Bly et al. | 424/49 |
| 3,376,198 A | * | 4/1968 | Petersen et al. | 167/78 |
| 3,657,413 A | | 4/1972 | Rosethal | |
| 3,886,265 A | * | 5/1975 | Evers et al. | 424/49 |
| 4,223,003 A | | 9/1980 | Scheller | |
| 4,324,782 A | * | 4/1982 | Beck | 424/87 |
| 4,405,599 A | | 9/1983 | Smigel | |
| 4,476,108 A | | 10/1984 | Kessler et al. | |
| 4,537,778 A | | 8/1985 | Clipper et al. | |
| 4,559,329 A | * | 12/1985 | Herschler | 514/164 |
| 4,693,888 A | * | 9/1987 | Miyahara et al. | 424/49 |
| 4,812,308 A | * | 3/1989 | Winston et al. | 424/53 |
| 4,839,157 A | | 6/1989 | Mei-King Ng et al. | |
| 4,971,782 A | * | 11/1990 | Rudy et al. | 424/53 |
| 4,978,521 A | * | 12/1990 | Blue | 424/49 |
| 5,817,294 A | * | 10/1998 | Arnold | 424/44 |
| 5,846,569 A | * | 12/1998 | Anderson et al. | 424/435 |
| 5,993,867 A | * | 11/1999 | Rohdewald | 426/96 |

FOREIGN PATENT DOCUMENTS

| | | | |
|---|---|---|---|
| EP | 0743060 A1 | * | 11/1996 |
| WO | 98/51316 a1 | * | 11/1998 |

* cited by examiner

*Primary Examiner*—Shep K. Rose
(74) *Attorney, Agent, or Firm*—Malin, Haley & DiMaggio, P.A.

(57) ABSTRACT

A anhydrous tooth and gum powdered dentifrice formulated of calcium or magnesium peroxide, sodium bicarbonate, methylsufonymethane, ascorbic acid, colostrum, and optionally menthol, flavoring agent, sweetening agent, sodium laurel sulfate and green tea extract that has a long shelf life but when activated by water or saliva, functions to effect a synergistic chemical and mechanical action to whiten, brighten, polish teeth and reduce bacteria so as to aid in the prevention and treatment of periodontal disease, dental caries and mouth odor.

3 Claims, No Drawings

ORAL HYGIENE POWDER COMPOSITION AND METHOD

BACKGROUND OF THE INVENTION

1. Field of the Invention

The invention relates to a storable, normally inactive, anhydrous oral dentifrice which promotes oral hygiene and which is activated by saliva and/or water, then applied onto the surface of teeth and adjacent gum tissues. The composition and method includes calcium or magnesium peroxide, sodium bicarbonate, ascorbic acid, methylsulfonymethane, and colostrum which are believed to function synergistically to cosmetically whiten, brighten, and bleach (to make whiter or lighter) teeth and therapeutically to cleanse the teeth and surrounding oral tissues and to kill the bacteria which contribute to the formation of dental plaque, caries, and mouth odor. Optionally green tea extract, sodium laurel sulfate, flavors, and sweeteners may be added.

2. Description of Related Art

The desire of people to have white teeth has been present in our society for decades. This desire is heightened by the presence of stains on teeth caused from the food we eat, smoking tobacco, medications, and poor oral hygiene, just to name a few. Many materials, compositions and processes have been developed over the years in attempts to solve this problem. These approaches are not without drawbacks, the most common being product instability, cost, product harshness to teeth and gums, specially trained personnel being required for product application, necessity of wearing specially crafted dental appliances often referred to as "splints". Thus, it is clear that a need exists for a tooth whitener and cleanser that is stable until use, reasonably priced, safe, easy to use, requires no special apparatus or trained personnel to apply, is not harmful to teeth, gums, and other surrounding tissues, and combats tooth and gum diseases commonly caused by bacteria.

To a large degree, dental caries and periodontal disease are connected closely to the formation of dental plaque. The literature has long reported that a majority of the world's population suffers from periodontal disease. According to the Merck Manual, 14th ed. 1982, P. 2104, the most common types of periodontal disease are gingivitis and periodontitis. Gingivitis (early stage gum disease) is an inflammation of the gums, characterized by swelling, redness, change in normal contours, and bleeding. If gingivitis is allowed to progress, periodontitis (late, stage gum disease), characterized by loss of tooth-supporting bone, will follow. The greatest single source of periodontal disease is poor hygiene, indicated by the appearance of bacterial and calcified plaque.

Dental plaque consists of a thin layer of mucilaginous film which is subject to invasion by colonizing bacteria. These bacteria in the presence of dietary carbohydrates lead to the production of acids which demineralize tooth enamel and dentine, attack gum tissue causing gingivitis (inflammation of the tissue surrounding the teeth) and react with the calcium in the teeth. Alkaline compounds such as sodium bicarbonate (baking soda) have been suggested in the art to neutralize plaque acids in order to inhibit caries formation and reduce demineralization of tooth enamel.

It, has long been known that bacteria play a part in pathogenic dental caries. Over the years, an abundance of research has implicated anaerobic bacteria as the causative agents of periodontal disease. Armitage, G. C., Biological Basis of Periodontal Maintenance Therapy, 1980. Anaerobic bacteria thrive only in the absence of oxygen. By providing high levels of oxygen, peroxides are believed to be effective in killing these bacterial organisms. The dental profession has considered many bacterial compounds over the years for their efficacy in preventing and treating periodontal diseases, peroxide being among them.

The Ng et al. U.S. Pat. No. 4,839,156, noted that peroxy compounds have long been recognized as effective against plaque and gingivitis. Peroxide preparations inhibit colonization and multiplication of the bacteria often associated with dental plaque and periodontal disease and also function as bleaching agents to whiten stained or discolored teeth.

Peroxides are known to be effective in curative and preventative treatments related to caries, dental plaque, gingivitis, periodontitis, mouth odor, tooth stains and oral lesions of the mucous membranes. In addition to treating periodontal disease, many individuals prefer using a combination of sodium bicarbonate and hydrogen peroxide to clean their teeth citing stain removal, a clean feeling, reduced mouth odor, and healthy gums as additional benefits. Sodium bicarbonate is particularly convenient, palatable and non-toxic. A mixture of approximately 60% sodium bicarbonate paste with a 3% solution of hydrogen peroxide has been used to treat periodontal disease.

The Winston et al, U.S. Pat. No. 4,812,308 created a stable composition in the form of a tooth powder mixture of sodium bicarbonate and sodium percarbonate. When the tooth powder makes contact with water, it releases active hydrogen peroxide. The percarbonate formulations generally have high pH in solution which could cause irritation of the gums and oral tissues.

Other sodium bicarbonate-containing and peroxide-releasing dentifrices incorporate enzymes for generating hydrogen peroxide in situ. See Kessler et al., U.S. Pat. No. 4,476,108. These enzyme induced hydrogen peroxide formulations, however, are so slow that only low levels of peroxide are produced during brushing.

Most peroxy compounds tend to be unstable in storage and hence lose their capacity to release the active or nascent oxygen which attacks the bacteria colonized plaque. As indicated in the Rosenthal U.S. Pat No. 3,657,413, it is the nascent oxygen which is believed to cause the antiseptic and/or cleansing effect of peroxide.

Various peroxide-releasing dentifrice formulations have been utilized over the years as oxidizing agents. For instance, urea peroxide has been used in combination with sodium bicarbonate, however, it is unstable and as a result preparations such as these require separate compartments of a container, increasing the cost of packaging.

The Scheller U.S. Pat. No. 4,223,003, discloses a dentifrice in a paste or powder form of magnesium peroxide as an oxidizing agent for removing film from teeth.

The Smigel U.S. Pat. No. 4,405,559, discloses a dental paste which combines calcium peroxide and sodium perborate as oxidizing agents to remove stains and plaque from teeth.

The Clipper et al. U.S. Pat. No. 4,537,778 discloses hydrogen peroxide in oral an aqueous oral composition for use as a mouthwash, rinse, gel or toothpaste.

U.S. Pat. No. 4,971,782 to Rudy a toothpaste or gel comprising a peroxide, bicarbonate, peroxide stabilizer, and non-aqueous hydrophilic vehicle. The present invention is a powder, not a paste or gel and does not include the non-aqueous, hydrophilic vehicle.

Dentifrice whitening products formulated with peroxide compounds normally do not contain abrasive polishing agents as such materials activate the rapid decomposition of the peroxide compounds whereby the oxygen is prematurely released. A disadvantage to the use of whitening products formulated without abrasives is that in addition to slow bleaching action, the products are not as effective in stain removal. Thus, the polishing agent incorporated in a dentifrice acts to debride and physically scrub the external surface of the teeth. This scrubbing action removes filmy bacterial and plaque layers, stains, discoloration and polishes the teeth to give the enamel a more lustrous appearance, higher optical sheen, and thus a brighter appearance.

None of the above prior art taken either alone or in combination, describes, suggests or renders obvious the instant invention as claimed.

BRIEF SUMMARY OF THE INVENTION

A chemically stable anhydrous tooth and gum dentrice is provided which is formulated principally of calcium or magnesium peroxide, sodium bicarbonate, ascorbic acid, methylsufonymethane, and colostrum which act synergistically to release oxygen for use to whiten, brighten, polish, and reduce bacteria in the oral cavity so as to reduce tooth decay, gum disease, and mouth odor. The present composition is sufficiently stable, that is, oxygen release is effectively inhibited, to allow storage of the mixture between usages thereby eliminating the previous need to construct separate compartment storing packages and provides increased oxygen-liberating capability. The stabilized oral hygiene composition formulation provides mechanical and oxidative mechanisms operate to destroy bacteria. The ascorbic acid functions not only to stabilize the peroxide but also increases the kinetic releases of oxygen by the mixture in coordination with the colostrum. The mechanical action of oxygen release is therefore increased to more effectively remove tissue and debris from the use environment.

In view of the above, one of the objects of this invention is to provide an effective, safe, and easily applied oral hygiene composition, inactive when stored but use activated functions to bleach, brighten, and whiten tooth enamel while combating the bacteria associated with dental plaque, caries, and bad breath.

Another object of this invention is to provide a method for hygienically treating humans for dental diseases comprising dental caries, gingivitis and periodontal in the oral cavity.

Another object of the present invention is to provide a stable peroxide-releasing tooth powder.

It is also an object of the invention to provide a dentifrice to control tooth, mouth and periodontal conditions and disease by synergistic chemical and mechanical actions.

These objects are attained in an oral hygiene composition which when brushed on or otherwise applied to the teeth and surrounding oral cavity tissues acts not only to bleach the teeth, but also to improve the condition of the gums and surrounding tissues. The invention also provides a method for bleaching, whitening, brightening, cleansing, and polishing the teeth and disinfecting the surrounding tissues using said formulation, wherein said formulation is applied to the teeth and surrounding oral cavity areas using a toothbrush or similar applicator.

In accordance with these and other objects which will become apparent hereinafter, the instant invention will now be described with particular reference to the accompanying drawings.

DETAILED DESCRIPTION OF THE INVENTION

An oral hygiene composition in accordance with the invention for releasing active oxygen is preferably in the form of an anhydrous powder so that it may be brushed or otherwise applied to the surface of the teeth and to adjacent gingival tissue and permitted to remain on the surfaces for up to several minutes, during which time active oxygen is released to bleach the enamel of the teeth and simultaneously oxidize and destroy bacteria commonly associated with dental plaque.

The composition of the present invention includes calcium or magnesium peroxide, sodium bicarbonate, methylsulfonymethane, ascorbic acid and colostrum. The calcium or magnesium peroxide, when activated, releases active oxygen to bleach and remove stains and mechanically remove debris from and around teeth surfaces and to whiten and brighten them while simultaneously oxidizing and destroying bacteria associated with dental plaque, caries, and gum disease.

The sodium bicarbonate, is a mild abrasive, cleanser, polisher, and breath freshener and renders alkaline, the pH of the composition when brushing the teeth. The sodium bicarbonate allows for long term use without damaging enamel surfaces or sensitive surrounding tissues. The composition is activated only when the composition is in the presence of water or saliva.

The present invention also includes methylsulfonymethane, a naturally occurring compound containing sulfur, which is a mineral necessary to the human immune system. The role of sulfur in the invention is believed to increase the permeability of the cell membranes such that water and oxygen flow more freely into the cells. In addition, the methylsulfonymethane possesses anti-inflammatory activity helpful in treating gingivitis, an inflammatory condition of the gums.

Ascorbic acid (vitamin C) in the present invention acts as an acidifier to assist in the release of oxygen from the peroxide. Ascorbic acid is a powerful antioxidant helpful in preventing free radical related cell damage and reduces the instability of the peroxide in the composition. It is also a vitamin important to the human body's disease resistance.

Colostrum, another component of the invention, is a lactation product produced by the mammalian mother for 5–7 days after giving birth and is a naturally occurring source of immunoglobulins. Immunoglobulins are high molecular weight proteins produced in the bodies of mature animals that enhance immunity to infection by bacteria, viruses, fungi, protozoa and the like. Colostrum has a particularly high concentration of a component of gamma globulin known as IgA, derived from cow's milk and known to attack bacteria and prevent local infection of the mucosal membranes of the mouth, throat, etc., see: Hanson, Lars A. et al, 1998, "Antiviral and Antibacterial Factors in Human Milk", in Lars A. Hanson, ed. Biology of Human Milk, Nestle Nutrition Workshop Series, Vol. 15, Raven Press, New York. Colostrum is recognized as having high protein and mineral content with antibacterial activity and enzymes, such as lactoperoxidasethiocyanate plus peroxidase and xanthine oxidase which oxidize bacteria by generating and releasing hydrogen peroxide. Colostrum's natural antimicrobial and immunological effects are enhanced synergistically by the oxygen generated by the saliva-activated calcium or magnesium peroxide and thus more readily available to treat and prevent the common dental conditions referred to above. The immunologic activity of colostrum is noted in Anderson, et al U.S. Pat. No. 5,846,569 and Graham U.S. Pat. No. 5,780,028.

Although the active oxygen will be released from the peroxide without ascorbic acid, the ascorbic acid acts as an acidifier to assist in the release, of oxygen from the peroxide and the colostrum enhances the overall anti-bacterial action and acts as a source of immunoglobulins necessary to prevent localized infections of the membranes and tissues of the mouth.

The following are compositions exemplary of the present invention in percent by weight of the total, but which should not be construed to limit the scope of the invention.

| Ingredient | #1 | #2 | #3 | #4 |
|---|---|---|---|---|
| Sodium Bicarbonate | 30.0% | 45.0% | 25% | up to 95% |
| Calcium or Magnesium Peroxide | 30.0% | 15.0% | 50% | up to 65% |
| Ascorbic Acid | 15.0% | 15.0% | 15% | up to 18% |
| Methylsulfonymethane | 7.5% | 7.5% | 7.5% | up to 9.0% |
| Colostrum | 1.0% | 1.0% | 1.0% | up to 5% |
| Green Tea Extract 40% | 1.7% | 1.7% | — | up to 3% |
| Sodium Laurel Sulfate | 15.0% | 15.0% | — | up to 15% |
| Aspartame | 0.3% | 0.3% | 0.5% | up to 5% |
| Peppermint powder | 0.3% | 0.3% | 0.5% | up to 5% |
| Menthol | 0.2% | 0.2% | 0.5% | up to 5% |
|  | 100% | 100% | 100% | 100% |

The tooth powder of the present invention is provided comprising up to 65% by weight of calcium or magnesium peroxide, up to 95% by weight of sodium bicarbonate, up to 18% by weight ascorbic acid, up to 9% methylsulfonymethane, up to 5% colostrum by weight, up to 15% sodium laurel sulfate, up to 3% green tea extract, up to 5% by weight sweetener, up to 5% by weight flavoring agent and up to 1% menthol. The preferred formulation is, however, set forth in #1 in the table above. The preferred ratio of calcium peroxide and sodium bicarbonate is 1:1, however ratios in excess of that can be utilized but it is though to decrease the stability of the peroxide.

Another embodiment of the invention eliminates the surfactant (sodium laurel sulfate) and the green tea extract, depending upon whether the purpose would include the anti-carcinogenic effect thought to be associated with green tea and whether foaming produced by the action of the surfactant is desired.

In another alternate embodiment, the method of whitening, brightening, cleansing, polishing teeth and disinfecting and treating surrounding gums and tissues is employed and comprises:
  a. combining then storing together calcium or magnesium peroxide sodium bicarbonate, ascorbic acid, methysulfonymethane and colostrum in a portable closed container, all powders being suitable for oral use;
  b. dampening a toothbrush or similar applicator with water;
  c. placing an effective amount of said anhydrous combination in contact with said toothbrush or similar applicator;
  d. brushing the teeth and surrounding tissues in the oral cavity using said composition, swishing said composition around in the mouth and thereafter expectorating the composition, and
  e. rinsing the mouth with water.

The components of this invention may contain other functional agents such as anti-inflammatory agents, acidifying agents, and immuno-supportive agents and mineral containing agents or sources. The present invention incorporates some or all of these agents.

1. Method of Manufacture

In preparing the composition, the ingredients in powder form are measured and mixed together. It is important to note that the prepared composition is inactive and stable, however, when the composition is applied orally and rendered acidic by saliva in the mouth, only then does it proceed to release active oxygen.

While there has been disclosed a preferred composition, it is to be understood that changes may be made therein without departing from the invention. Thus different sweeteners and flavoring agents other than those disclosed herein may be employed.

2. Composition's Use

The composition of the present invention is used in powder form generally in an amount from about 0.2 g to about 0.3 g per serving. The composition is placed in the hand or directly onto a wet toothbrush or similar applicator and applied to teeth by brushing in the customary manner, for a period from 60 seconds to 120 seconds, preferably from about 100 seconds to 150 seconds.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An anhydrous oral hygiene dentifrice powder composition consisting of:
  a. calcium peroxide, 30% by weight;
  b. sodium bicarbonate, 30% by weight;
  c. methylsulfonymethane, 7.5% by weight;
  d. ascorbic acid, 15% by weight;
  e. colostrums, 1% by weight;
  f. sodium lauryl sulfate, 15% by weight;
  g. green tea extract, 1.7% by weight;
  h. sweetner, 0.3% by weight;
  i. methol, 0.2% by weight; and
  j. flavor, 0.3% by weight.

2. A method for whitening, brightening, cleansing, polishing teeth and disinfecting and treating surrounding gums and tissues comprising:
  a. combining then storing together the ingredients according to claim 1 in a portable closed container, all powders being suitable for oral use;
  b. dampening a toothbrush or similar applicator with water;
  c. placing an effective amount of said anhydrous combination in contact with said toothbrush or similar applicator;
  d. brushing the teeth and surrounding gums and tissues in the oral cavity using said composition, swishing said composition around in the mouth and thereafter expectorating the composition;
  e. rinsing the mouth with water.

3. A method for whitening, brightening, cleansing, polishing teeth and disinfecting and treating surrounding gums and tissues comprising:
  a. combining then storing together the ingredients according to claim 1 in a portable closed container, all powders being suitable for oral use;
  b. dampening a toothbrush or similar applicator with water;

c. placing an effective amount of said anhydrous combination in contact with said toothbrush or similar applicator;

d. brushing the teeth and surrounding gums and tissues in the oral cavity using said composition, swishing said composition around in the mouth and thereafter expectorating the composition;

e. rinsing the mouth with water.

* * * * *